US00PP19844P2

(12) United States Plant Patent
Horvath

(10) Patent No.: US PP19,844 P2
(45) Date of Patent: Mar. 24, 2009

(54) ***LOBELIA* PLANT NAMED 'GOLDEN TORCH'**

(50) Latin Name: *Lobelia cardinalis*
Varietal Denomination: Golden Torch

(76) Inventor: Brent Horvath, c/o Intrinsic Perennial Gardens, Inc. 10702 Seaman Rd., Hebron, IL (US) 60034

( * ) Notice: Subject to any disclaimer, the term of this patent is extended or adjusted under 35 U.S.C. 154(b) by 0 days.

(21) Appl. No.: 12/011,153

(22) Filed: Jan. 23, 2008

(51) Int. Cl.
*A01H 5/00* (2006.01)

(52) U.S. Cl. ..... Plt./451

(58) Field of Classification Search ..... Plt./451
See application file for complete search history.

*Primary Examiner*—Annette H Para
(74) *Attorney, Agent, or Firm*—Klarquist Sparkman, LLP

(57) ABSTRACT

A new and distinct *Lobelia cardinalis* plant characterized by yellow to lime green foliage.

1 Drawing Sheet

Botanical denomination: *Lobelia cardinalis.*
Variety designation: 'Golden Torch'.

BACKGROUND OF THE INVENTION

The present invention relates to a new and distinct cultivar of *Lobelia* and given the cultivar name of 'Golden Torch'. *Lobelia* is in the family Campanulaceae. *Lobelia cardinalis* 'Golden Torch' originated as a seedling from a *Lobelia cardinalis* sowing.

Compared to *Lobelia cardinalis,* the new cultivar has yellow foliage rather than green. This is the first known yellow foliage *Lobelia cardinalis.*

This new cultivar has been reproduced only by asexual propagation (tip cuttings and tissue culture). Each of the progeny exhibits identical characteristics to the original plant. Asexual propagation by division and tissue culture using standard micropropagation techniques with terminal and lateral shoots, as done in Canby, Oreg. shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The photo shows a two-year-old plant of *Lobelia* 'Golden Torch' growing in the ground in full sun in the trial field in August in Canby, Oreg.

DETAILED PLANT DESCRIPTION

The following is a detailed description of the new *Lobelia* cultivar based on observations taken in August of a one-year-old specimen growing in the ground in the trial bed in full sun with added irrigation in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Form.*—Herbaceous perennial.
- *Hardiness.*—USDA Zone 3 to 9.
- *Size.*—45 cm to 80 cm tall from top of the flower to the ground and 30 cm to 40 cm wide.
- *Habit.*—Upright.
- *Vigor.*—Excellent.

Basal leaf:
- *Type.*—simple.
- *Arrangement.*—Rosulate.
- *Shape.*—Narrowly ovate.
- *Venation.*—Pinnate.
- *Margins.*—Toothed.
- *Apex.*—Obtuse to acute.
- *Base.*—Attenuate.
- *Blade size.*—5.5 cm long and 2.5 cm wide.
- *Petiole.*—3 cm long and 2 mm wide, Yellow Green 145B, glabrous.
- *Surface texture.*—Glabrous on both sides.
- *Leaf color.*—Topside, Yellow 12C in the spring to Yellow Green 144B in the summer; bottom side same.

Cauline leaf:
- *Type.*—Simple.
- *Arrangement.*—Alternate.
- *Shape.*—Oblong lanceolate.
- *Venation.*—Pinnate.
- *Margins.*—Toothed.
- *Apex.*—Acuminate.
- *Base.*—Attenuate.
- *Blade size.*—5 cm to 11 cm long and 2 cm to 3.5 cm wide.
- *Surface texture.*—glabrous on top sides, sparsely pubescent on veins on bottom side.
- *Petiole.*—Sessile.
- *Leaf color.*—Topside, Yellow 12C in the spring to Yellow Green 144B with areas of Yellow 12B interveinally in the summer; bottom side same.

Inflorescence:
- *Size.*—About 5 cm wide and 12 cm to 36 cm long.
- *Type.*—Bracteate spike.
- *Number of flowers per spike.*—25 to 55.
- *Number of spikes in flowering season.*—5.

*Peduncle.*—45 cm to 85 cm tall, 6 mm wide at base, Yellow Green 144A, internodes 7 mm to 20 mm long, sparsely pubescent.

*Pedicel.*—10 mm long, Yellow Green 144A, sparsely pubescent.

*Bloom period.*—Beginning of August through middle of September in Canby, Oreg.

*Lastingness.*—Each spike blooms for about 3 weeks.

Flower bud:

*Size.*—5 mm wide and 3 cm long.

*Description.*—Glandular puberulent, tubular.

*Color.*—Red 53A to 53B.

Flower:

*Type.*—Perfect.

*Shape.*—Bilabiate, lower three lobes spreading, upper 2 lobes recurved.

*Size.*—3.5 cm long and 2 cm wide.

*Corolla description.*—Tube 13 mm long and 5 mm wide, 5 lobes, lower three cut ⅓ to ⅔ of their length, each 10 mm long and 4 mm wide, elliptic, tip acute, margin entire, glabrous on both sides, Red 53A on top side and Red 53B on bottom side.

*Calyx description.*—Campanulate over ovary with 5 long narrow lobes around the corolla, each lobe 14 mm long and 1 mm wide, with 5 lobes, divided ½ way to the base, tip acuminate, margin entire, glabrous on both sides, Green 138A inside and Green 138A tinted Greyed Purple 185A on outside lobe tips.

*Stamen description.*—5 in number, overall 33 mm long and 5 mm wide; filaments fused and flatted, encircling style, each filaments 28 mm long and about 1 mm wide, Red 53A on top third, Red 54C on middle third lightening to White 155A at the base, anthers fertile, 4 mm long, Greyed Purple 187A to maturing to Grey 201A; pollen Yellow 11A.

*Pistil description.*—1 in number, 35 mm long; ovary 7 mm long and 5 mm wide, Yellow Green 144B; style 30 mm long, Red 53B, stigma Black 202A surrounded by white hairs.

*Fragrance.*—None.

Fruit:

*Type.*—Ovoid capsule.

*Size.*—1 cm wide.

*Fertility.*—Good.

*Color.*—Brown 200D.

Seed:

*Shape.*—Warty ovoid.

*Size.*—1 mm.

*Color.*—Grey Brown 199A.

Pest and disease tolerance: No known pest or disease resistances.

I claim:

1. A new and distinct *Lobelia* plant as herein illustrated and described.

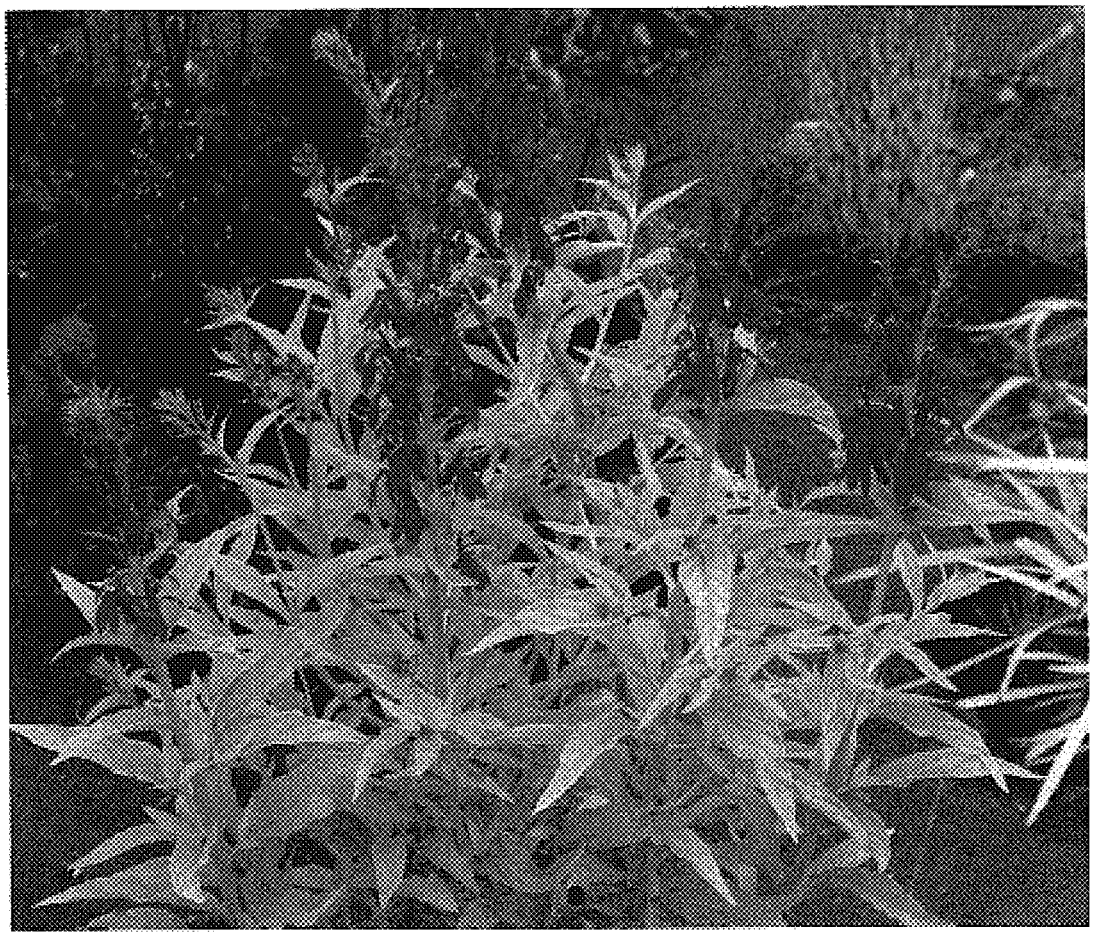

* * * * *